(12) United States Patent
Holt et al.

(10) Patent No.: US 9,839,535 B2
(45) Date of Patent: Dec. 12, 2017

(54) MODULAR PROSTHETIC ABUTMENT SYSTEM

(71) Applicant: UNIVERSITY OF UTAH RESEARCH FOUNDATION, Salt Lake City, UT (US)

(72) Inventors: Brian Mueller Holt, Topanga, CA (US); Sujee Jeyapalina, Salt Lake City, UT (US); Roy Drake Bloebaum, Salt Lake City, UT (US); Kent Nelson Bachus, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 62 days.

(21) Appl. No.: 14/415,939

(22) PCT Filed: Jul. 19, 2013

(86) PCT No.: PCT/US2013/051375
§ 371 (c)(1),
(2) Date: Jan. 20, 2015

(87) PCT Pub. No.: WO2014/015303
PCT Pub. Date: Jan. 23, 2014

(65) Prior Publication Data
US 2015/0182356 A1    Jul. 2, 2015

Related U.S. Application Data

(60) Provisional application No. 61/673,924, filed on Jul. 20, 2012, provisional application No. 61/709,756, filed on Oct. 4, 2012.

(51) Int. Cl.
*A61F 2/28* (2006.01)
*A61F 2/30* (2006.01)
(Continued)

(52) U.S. Cl.
CPC .............. *A61F 2/78* (2013.01); *A61F 2/2814* (2013.01); *A61F 2002/3055* (2013.01);
(Continued)

(58) Field of Classification Search
CPC .. A61F 2/2814; A61F 2/78; A61F 2002/5083; A61F 2002/7887;
(Continued)

(56) References Cited

U.S. PATENT DOCUMENTS 3,947,897 A   4/1976 Owens
4,158,895 A   6/1979 Frosch et al.
(Continued)

FOREIGN PATENT DOCUMENTS

DE       19931882 C1    5/2001
DE    202004014043 U1   12/2004
(Continued)

OTHER PUBLICATIONS

U.S. Appl. No. 13/123,719, filed Feb. 10, 2014, Holt et al.
(Continued)

*Primary Examiner* — Thomas J Sweet
*Assistant Examiner* — Christie Bahena
(74) *Attorney, Agent, or Firm* — Ballard Spahr LLP

(57) ABSTRACT

An abutment system for operatively coupling an implant stem to an exo-prosthesis. The abutment system includes a plurality of interlocking sleeve elements that are operatively coupled to an implant stem positioned within a prepared site of a selected bone. The interlocking sleeve elements of the abutment system are selectively removable and replaceable.

28 Claims, 15 Drawing Sheets

(51) Int. Cl.
*A61F 2/50* (2006.01)
*A61F 2/78* (2006.01)

(52) U.S. Cl.
CPC . *A61F 2002/502* (2013.01); *A61F 2002/5083* (2013.01); *A61F 2002/7887* (2013.01); *A61F 2220/0041* (2013.01)

(58) Field of Classification Search
CPC ............. A61F 2220/0033; A61C 8/001; A61C 8/0039; A61C 8/0042; A61C 8/0043; A61C 8/0045
See application file for complete search history.

(56) References Cited

U.S. PATENT DOCUMENTS

| | | | |
|---|---|---|---|
| 4,872,840 A * | 10/1989 | Bori | A61C 3/16 433/173 |
| 4,938,769 A | 7/1990 | Shaw | |
| 5,833,664 A * | 11/1998 | Seare, Jr. | A61M 25/04 604/174 |
| 5,906,644 A | 5/1999 | Powell | |
| 6,869,450 B2 | 3/2005 | Grundei | |
| 7,909,883 B2 | 3/2011 | Sidebotham | |
| 2002/0038148 A1 | 3/2002 | Fernandez et al. | |
| 2003/0109878 A1 | 6/2003 | Grundei | |
| 2004/0068324 A1 | 4/2004 | Grundei | |
| 2005/0102038 A1 | 5/2005 | Grundei | |
| 2005/0214714 A1 | 9/2005 | Wohrle | |
| 2007/0060891 A1 * | 3/2007 | Skiera | A61F 2/2814 604/175 |
| 2009/0005820 A1 * | 1/2009 | Bloebaum | A61F 2/2814 606/302 |
| 2009/0187256 A1 | 7/2009 | Rauguth et al. | |
| 2010/0082103 A1 * | 4/2010 | Blunn | A61F 2/2814 623/13.14 |
| 2010/0222893 A1 | 9/2010 | Dorr et al. | |
| 2011/0189634 A1 * | 8/2011 | Kfir | A61C 8/0018 433/174 |
| 2011/0190907 A1 | 8/2011 | Porter et al. | |
| 2011/0257758 A1 | 10/2011 | Smith et al. | |
| 2013/0006356 A1 * | 1/2013 | Cook | A61F 2/78 623/16.11 |
| 2013/0195540 A1 * | 8/2013 | Wozencroft | A61F 2/78 403/83 |
| 2014/0156022 A1 | 6/2014 | Holt et al. | |
| 2014/0195002 A1 | 7/2014 | Bachus et al. | |

FOREIGN PATENT DOCUMENTS

| | | |
|---|---|---|
| DE | 102009027255 A1 | 8/2010 |
| DE | 102010028964 A1 | 11/2011 |
| EP | 1649834 A1 | 4/2006 |
| WO | WO-95/13028 A1 | 5/1995 |
| WO | WO-2006/084346 A1 | 8/2006 |
| WO | WO-2009/105535 A1 | 8/2009 |

OTHER PUBLICATIONS

U.S. Appl. No. 14/181,029, filed Feb. 14, 2014, Bachus et al.
EP 13820604.0, filed Jul. 19, 2013, Holt et al.
PCT/US2013/051375, filed Jul. 19, 2013, Holt et al.
PCT/US2012/041112, filed Jun. 6, 2013, Holt et al.
AZoM, Titanium Alloys in Medical Applications, AZO Materials, The Titanium Information Group, UK, Jan. 2003 http://www.azom.com/article.aspx?ArticleID=1794 (4 pages).
Extended European Search Report was dated Apr. 19, 2016 by the European Patent office for Application No. 13820604.0, which was filed on Jul. 19, 2013 and published as 2874572 on May 27, 2015 (Inventor—Holt et al; Applicant—University of Utah) (6 Pages).
International Search Report was dated Dec. 6, 2013 for International Application No. PCT/US2013/051375, which was filed on Jul. 19, 2013 and published as WO2014/015303 on Jan. 23, 2014 (Inventor—Holt et al; Applicant—University of Utah) (2 Pages).
Written Opinion was dated Dec. 6, 2013 for International Application No. PCT/US2013/051375, which was filed on Jul. 19, 2013 and published as WO2014/015303 on Jan. 23, 2014 (Inventor—Holt et al; Applicant—University of Utah) (4 Pages).
International Search Report was dated Mar. 13, 2013 for International Application No. PCT/US2012/051375, which was filed on Jun. 6, 2012 and published as WO 2013/048589 on Apr. 4, 2013 ( Applicant—University of Utah) (2 Pages).
Written Opinion was dated Mar. 13, 2013 for International Application No. PCT/US2012/051375, which was filed on Jun. 6, 2012 and published as WO 2013/048589 on Apr. 4, 2013 ( Applicant—University of Utah) (7 Pages).

* cited by examiner

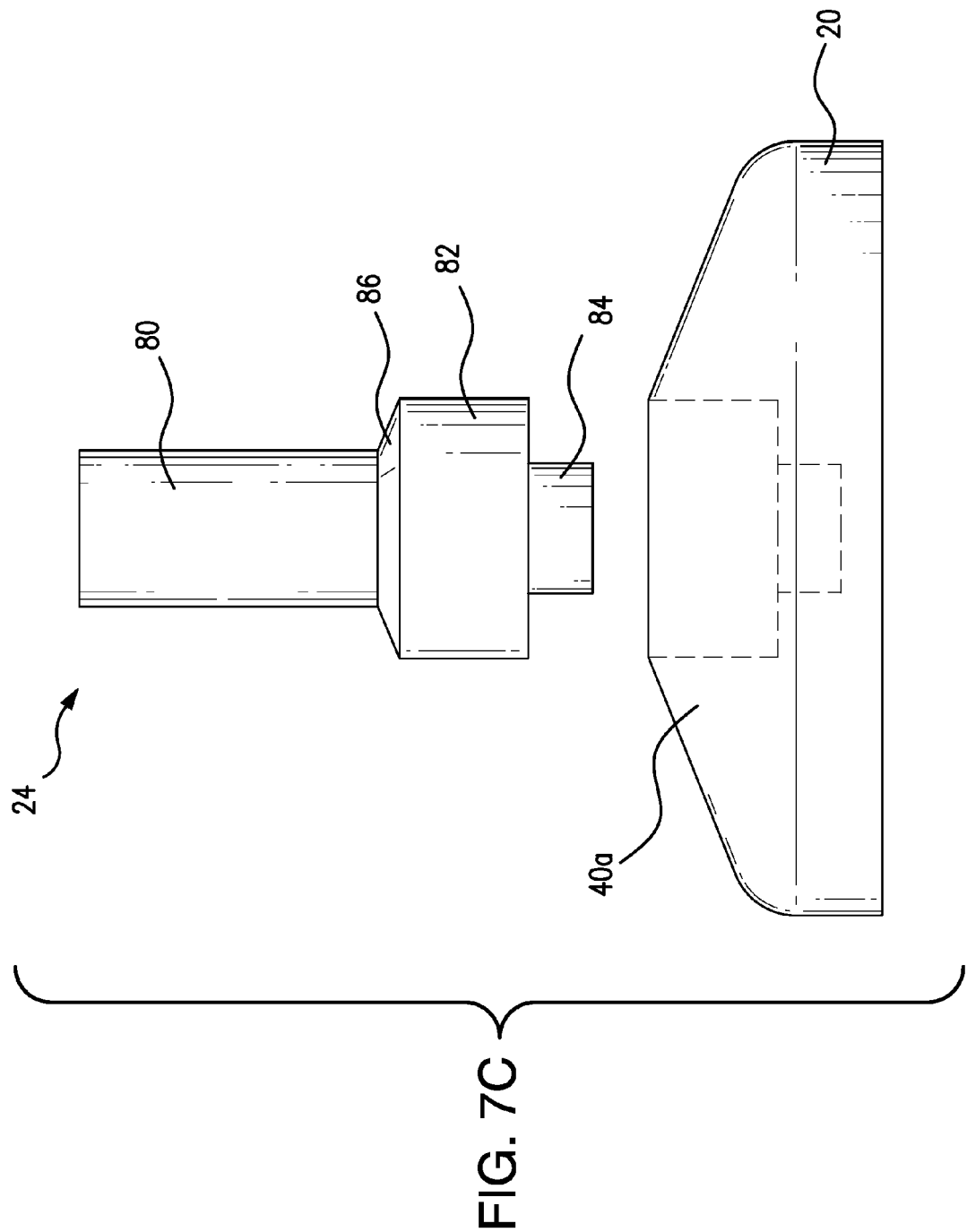

MODULAR PROSTHETIC ABUTMENT SYSTEM

CROSS-REFERENCE TO RELATED APPLICATIONS

This application claims benefit of priority under 35 U.S.C. §371 of International Application PCT/US2013/051375, filed on Jul. 19, 2013, which claims the benefit of priority of U.S. Provisional Patent Application No. 61/673,924, filed on Jul. 20, 2012, and U.S. Provisional Patent Application No. 61/709,756, filed on Oct. 4, 2012. The contents of the prior international and provisional applications are hereby incorporated by reference herein in their entirety.

STATEMENT OF GOVERNMENT SUPPORT

This invention was made with government support under W81XWH-06-1-0574 awarded by Army/MRMC—Medical Research and Materiel Command, and AR058356 awarded by National Institute of Health. The government has certain rights in the invention.

FIELD

This invention generally relates to percutaneous implant systems for securing a prosthesis to a selected bone of a subject, and, more particularly, to a modular abutment system for soft tissue fixation (securement) of a prosthetic system to a selected soft tissue of a subject.

BACKGROUND

A variety of known percutaneous fixation implants are currently used to couple a prosthesis to a selected bone of a subject. Typically, the fixation implants are positioned within the selected bone, and the prosthesis is securely attached to the fixation implant. Such percutaneous fixation implants are conventionally associated with many complications, including (a) infection at the fixation implant exit site (where the fixation implant exits the body of the subject), (b) skin regression/marsupialization/downgrowth (e.g., epidermal and/or dermal regression), and (c) failure of component materials.

To address these complications, the fixation implants, including abutment components, generally must be removed from the body of the subject and/or replaced. Additionally, in circumstances where any portion of the soft tissue fixation implant (abutment) is demonstrating mechanical failure or is contributing to the experienced complications, the entire fixation implant must be replaced. Thus, not only do the complications outlined above decrease the functionality of the fixation implants, but they also increase the frequency of at which the abutment and/or entire implant are replaced, thereby increasing health care costs and decreasing efficiency of patient treatment and therapy plans.

Accordingly, in view of the above-referenced limitations of conventional fixation implant abutments, what is needed in the art is an inherently adaptable, modular percutaneous abutment system that permits removal of only selected portions of the fixation implant and also permits replacement of the removed portions of the fixation implant with new, revised, and/or optimized components, thereby providing for adaptation of the soft tissue fixation component of the implant to changing patient conditions and increasing the longevity of the fixation implant and abutment system.

SUMMARY

The present invention relates to an abutment system for operatively coupling an implant stem to an exo-prosthesis, with the implant stem being configured for positioning within a prepared site of a selected tissue region of a subject. Optionally, the abutment system can include a base element having a flange and an elongate shaft. The flange of the base element can have a first surface, an opposed second surface, and an outer edge extending between the first and second surfaces, with the first surface of the flange defining a proximal end of the base element. The proximal end of the base element can be configured for operative coupling to the implant stem. The elongate shaft can extend from a central portion of the flange away from the proximal end of the base element relative to a common longitudinal axis of the abutment system.

The abutment system can also include a plurality of interlocking sleeve elements. Each sleeve element of the plurality of sleeve elements can define a central bore configured for receipt of the elongate shaft of the base element or, alternatively, receipt of a fixation bolt. The plurality of sleeve elements can comprise a proximal sleeve element and a distal sleeve element, with the proximal sleeve element being configured for engagement with the flange of the base element or, alternatively, engagement with an implant stem and/or limb of a subject. Each sleeve element of the plurality of sleeve elements can be configured for selective, removable engagement with adjacent sleeve elements of the plurality of sleeve elements.

The abutment system can further include an end cap configured for engagement with the distal sleeve element of the plurality of sleeve elements and for docking/attachment of one or more exo-prostheses. The end cap can have a proximal portion and a distal portion. The proximal portion and the distal portion of the end cap can have respective outer surfaces. The distal portion of the end cap can optionally define a closed distal end of the end cap. Alternatively, the end cap can define a bore configured to receive a fixation bolt.

Optionally, the elongate shaft of the base element can be integrally formed with the base element. Alternatively, the elongate shaft of the base element can be selectively detachable from the base element.

Kits incorporating the abutment system and methods of using the abutment system are also disclosed.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

FIG. 2 depicts various views of an exemplary base element of an abutment system as described herein.

FIG. 3 depicts various views of an exemplary proximal sleeve element of an abutment system as described herein.

FIG. 4 depicts various views of an exemplary intermediate sleeve element of an abutment system as described herein.

FIG. 5 depicts various views of an exemplary distal sleeve element of an abutment system as described herein.

FIG. 6 depicts various views of an alternative configuration for a base element and a proximal sleeve element of an exemplary abutment system as described herein.

FIG. 7 depicts various exploded views of the base element and proximal sleeve element of the exemplary abutment system depicted in FIG. 6. FIG. 7C depicts an exploded transparent side view of the base element and the proximal sleeve element.

DETAILED DESCRIPTION

Figure 1:
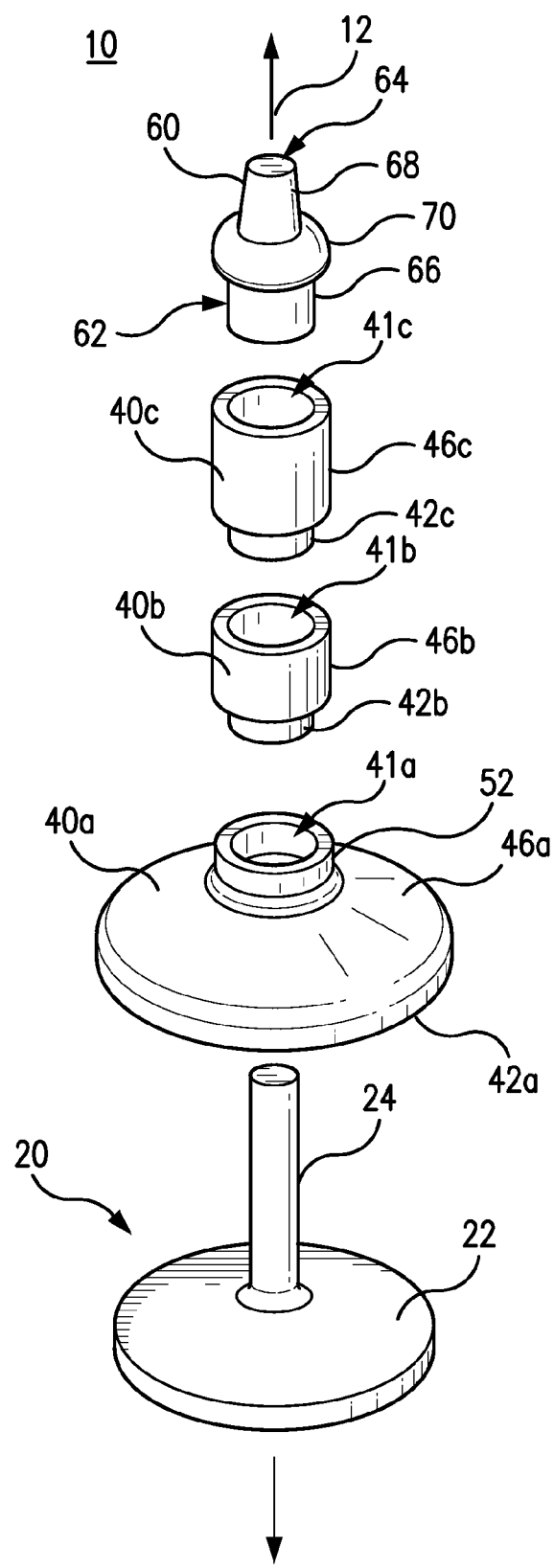
FIG. 1 depicts an exploded perspective view of an exemplary abutment system as described herein.
Figure 2A:
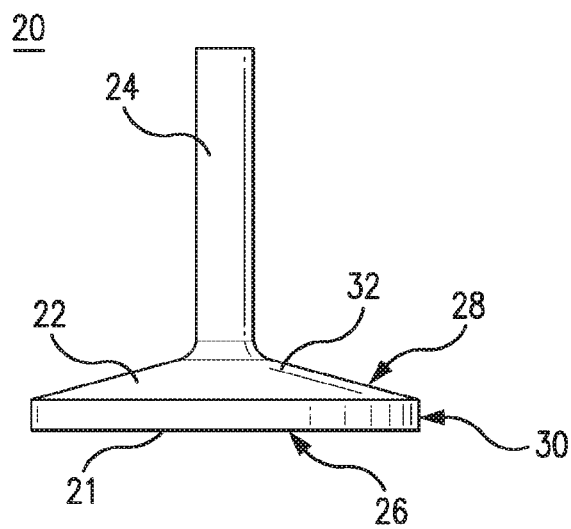
FIG. 2A depicts a side view of the base element.
Figure 2B:
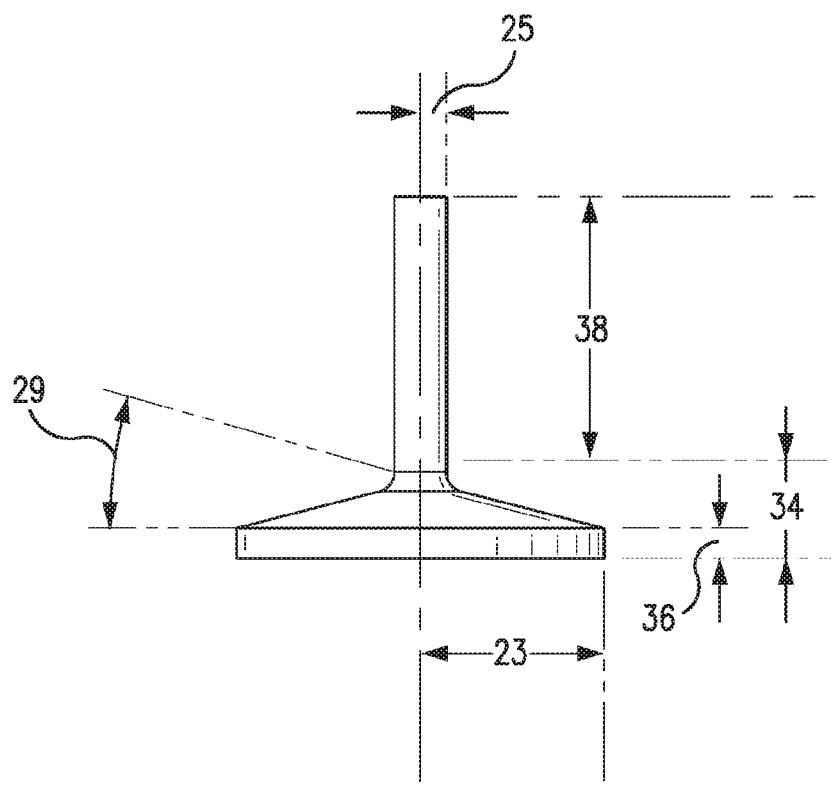
FIG. 2B depicts a partially transparent side view of the base element.
Figure 2C:
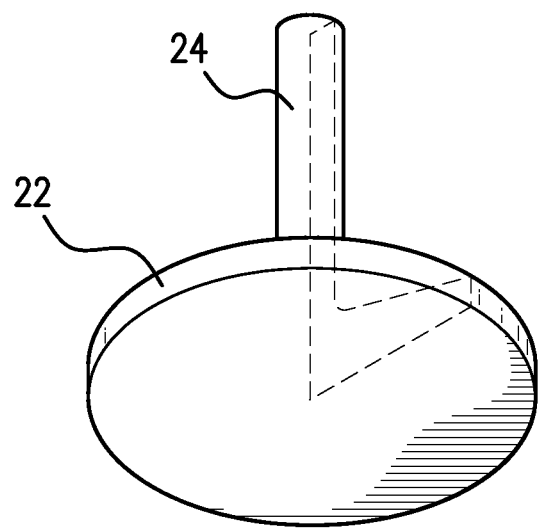
FIG. 2C depicts a partially transparent bottom perspective view of the base element.
Figure 2D:
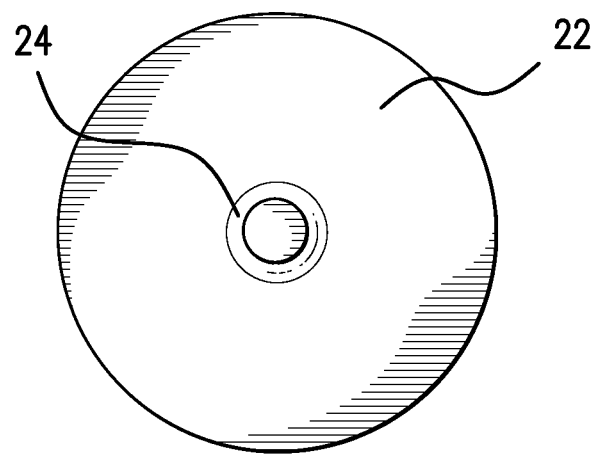
FIG. 2D depicts a top view of the base element.
Figure 3A:
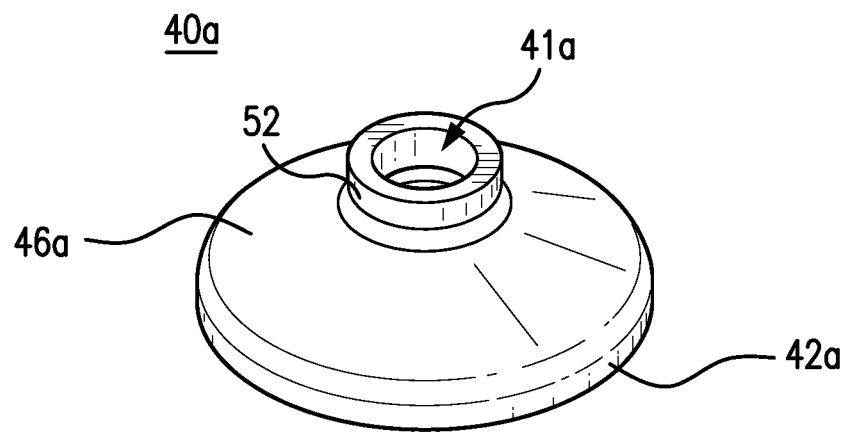
FIG. 3A depicts a perspective view of the proximal sleeve element.
Figure 3B:
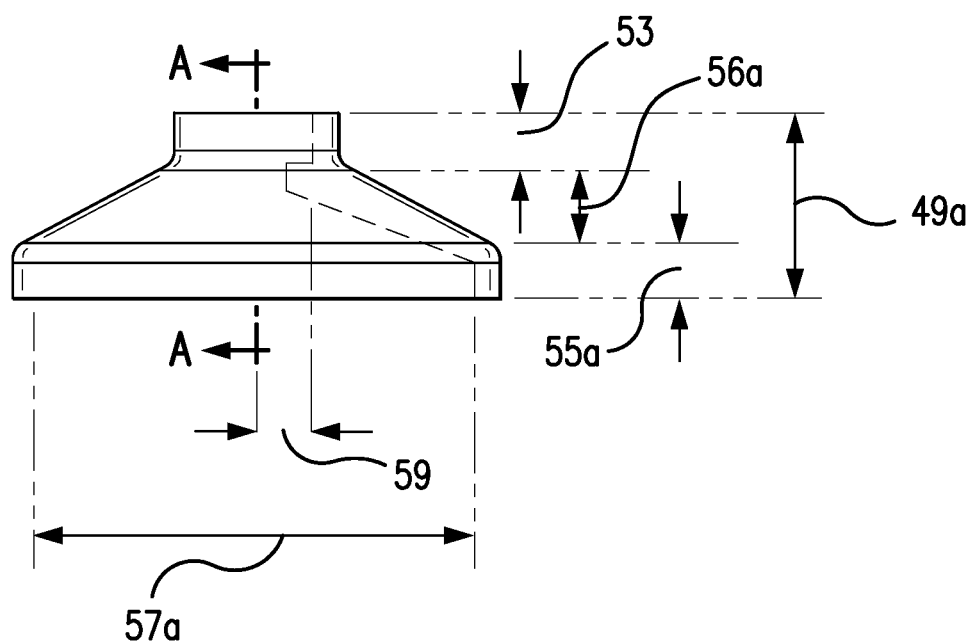
FIG. 3B depicts a side view of the proximal sleeve element.
Figure 3C:
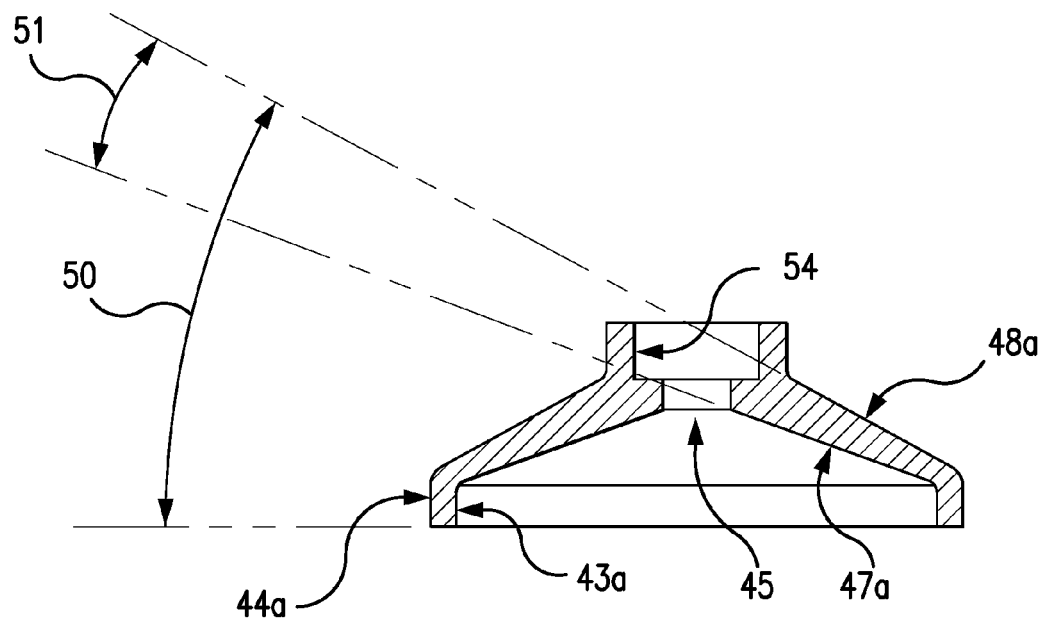
FIG. 3C depicts a cross-sectional view of the proximal sleeve element of FIG. 3B, taken at line A-A.
Figure 3D:
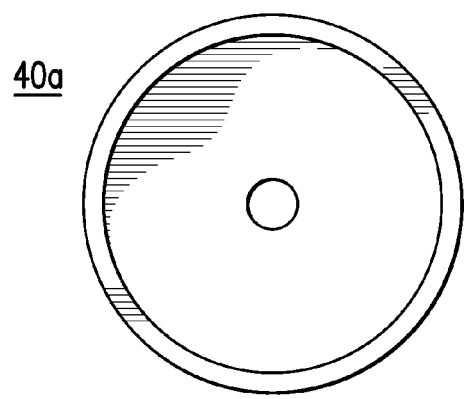
FIG. 3D depicts a top view of the proximal sleeve element.
Figure 4A:
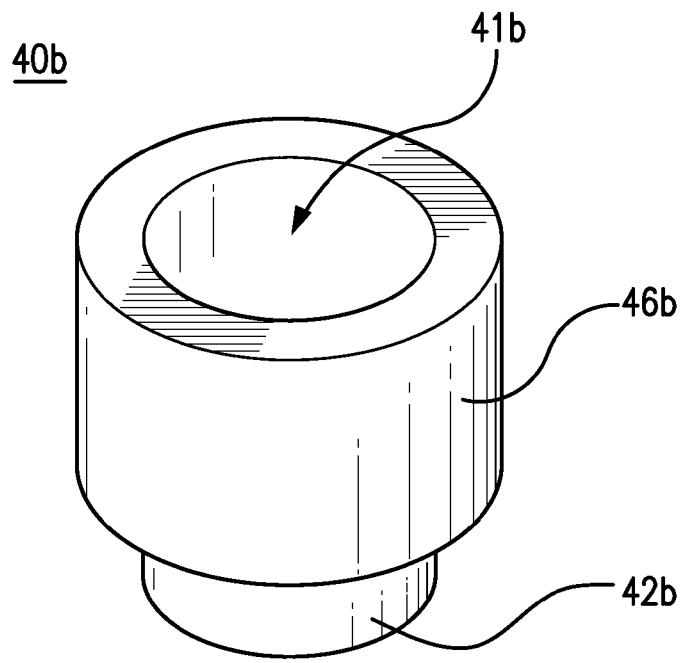
FIG. 4A depicts a perspective view of the intermediate sleeve element.
Figure 4B:
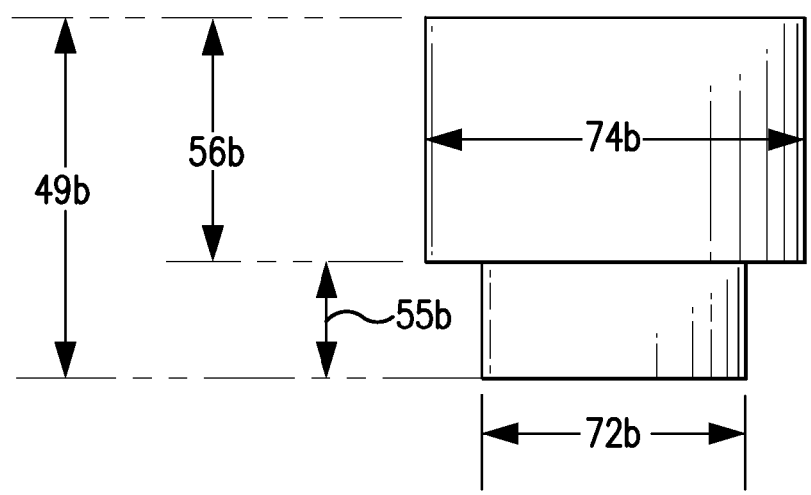
FIG. 4B depicts a side view of the intermediate sleeve element.
Figure 4C:
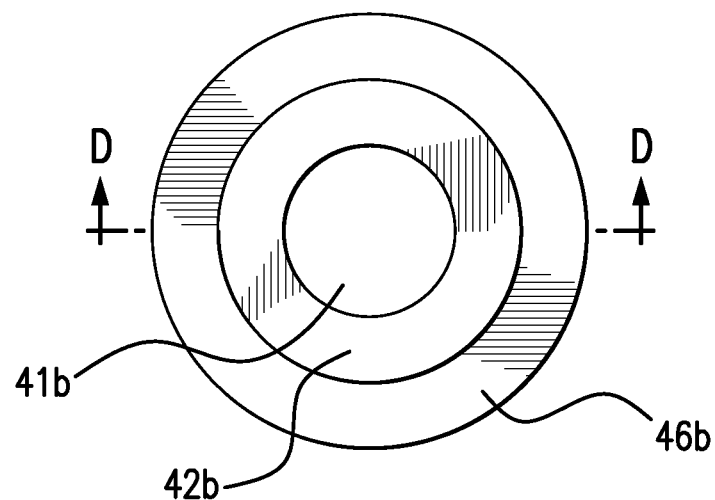
FIG. 4C depicts a top view of the intermediate sleeve element.
Figure 4D:
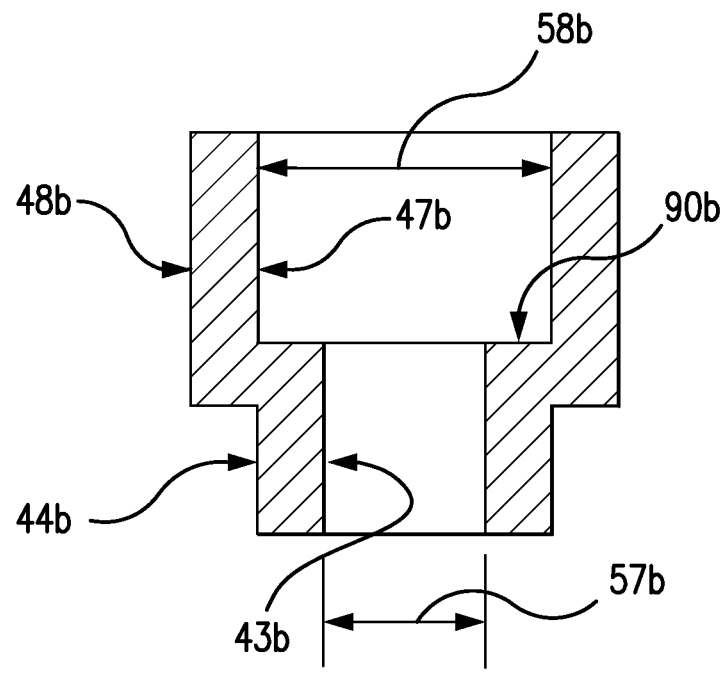
FIG. 4D depicts a cross-sectional view of the intermediate sleeve element of FIG. 4C, taken at line D-D.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a sleeve element" can include two or more such sleeve elements unless the context indicates otherwise.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject can include humans and can also include small or laboratory animals as well as primates. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

As used herein, the term "insertional" refers to the end of a first element that is configured for insertion into a second element. For example, as used herein, an "insertional" end of an element can be configured for insertion into a prepared site within a bone or for insertion into an implant stem.

As used herein, the term "proximal" refers to the portion of an element that is closest to the body of a subject when the element is operatively positioned according to its intended use.

As used herein, the term "distal" refers to the portion of an element that is farthest from the body of a subject when the element is operatively positioned according to its intended use.

As used herein, the term "ultra-low friction surface" refers to a surface comprising or coated with one or more materials that are configured to inhibit adhesion and/or adsorption between the surface and other materials. For example, "ultra-low friction surfaces" as described herein permit little if any in-growth, integration, and/or adhesion between the surface and biological tissues, biological fluids, and bacteria. It is contemplated that the reduced bio-adhesion permitted by the "ultra-low friction surfaces" as described herein can permit thorough post-operative drainage for improved wound healing, ease "at-home" cleaning, and reduce the incidence of infection. Exemplary ultra-low friction surfaces include surfaces that comprise or are coated with ultra-hydrophobic materials. Additional exemplary ultra-low friction surfaces include, for example and without limitation, gold, ceramics, polymers (e.g., ultra high molecular weight polyethylene), diamond-like carbon (DLC) coatings, oxidized zirconium, titanium nitride, and the like. It is contemplated that exemplary "ultra-low friction surfaces" as described herein can have coefficients of friction that are less than or equal to about 0.6. In some exemplary aspects, the "ultra-low friction surfaces" can have coefficients of friction that are less than or equal to about 0.01 (approaching superlubricity).

As used herein, the term "selected tissue region" refers to a selected bone within the body of a subject, as well as the soft tissue surrounding and/or adjacent to the selected bone. The term "selected tissue region" is intended to include all tissues of the subject that the abutment system (and implant components associated with the abutment system) contacts when used as described herein.

As used herein, a "prepared site" within a selected tissue region refers to a any formation, such as a channel and/or cavity, that is formed within the selected bone and/or surrounding soft tissue of the selected tissue region for purposes of receiving an implant, such as an OI implant as described herein, using conventional surgical methods.

Disclosed herein are abutment systems, as well as methods for securing a prosthesis to a limb of a subject. It is contemplated that the disclosed abutment systems and methods can be used to permit integration of the skin of the subject into an implant, to which a prosthesis is operably attached. It is further contemplated that the disclosed abutment systems and methods can permit formation of a seal between the skin of the subject and the implant, thereby minimizing the possibility of infection at the interface between the implant and the skin of the subject. It is still further contemplated that the disclosed abutment systems and methods can minimize post-implantation migration of the skin of the subject, thereby reducing the likelihood of formation of a pocket (sinus tract) between the skin of the subject and the implant. It is further contemplated that the disclosed abutment systems and methods can allow surgeons to remove and/or replace individual components of the abutment system with minimal disturbance to the bone-anchored portions of the implant system. For example, in use, it is contemplated that the disclosed abutment systems and methods can permit revision to the abutment system and/or adjacent soft tissue to alleviate and/or treat dermatological complications, including, for example and without limitation, infection, without the need for removal of an osseointegrated (OI) stem or other osseointegrated (OI) implant component used to anchor the overall system.

In particular applications, it is contemplated that the disclosed abutment systems and methods can be used to bring military, veteran and civilian lower-extremity amputees back to pre-amputation/improved activity levels. Generally, it is contemplated that the above-mentioned objectives can be achieved through optimized selection of various characteristics of the abutment system, such as, for example, characteristics of the materials of the various components of the abutment system, to achieve a desired arrangement and/or orientation of the components of abutment system relative to the bone and surrounding periprosthetic tissue of the subject. Following the securing of the prosthesis to the limb of the subject, it is contemplated that the various portions and components of the abutment systems disclosed herein can be selectively removed, altered, and/or replaced to achieve the desired arrangement and/or orientation of the components of the abutment system.

Referring to FIGS. 1-5 and 8, an abutment system 10 is provided for operatively coupling an implant stem to a prosthesis. As shown in FIG. 1, the elements of the abutment system 10 can have a common longitudinal axis 12. The implant stem is configured for positioning within a prepared site of a selected tissue region of a subject, such as, for example, a selected bone within an upper or lower extremity of a subject. In exemplary aspects, the prepared site can be an intramedullary cavity of a selected bone. In additional exemplary aspects, the selected bone can be a femur of the subject. However, it is contemplated that the disclosed methods, systems, and steps and components thereof can be used with any bone within a tissue region of a subject, including, for example, any bone within an upper or lower extremity of a subject. It is contemplated that the abutment system 10 can be used to secure a prosthesis to a prepared site within the selected bone. In exemplary, optional aspects, the implant stem can be configured to promote osseointegration. The assembled abutment system 10 can be configured for secure attachment to the prosthesis.

In exemplary aspects, the abutment system 10 can comprise a plurality of interlocking sleeve elements 40 and an end cap 60. In these aspects, and with reference to FIGS. 1, 3-5, and 8, the plurality of sleeve elements 40 can comprise a proximal sleeve element 40$a$ and a distal sleeve element 40$c$. In additional aspects, the plurality of interlocking sleeve elements 40 of the abutment system 10 can each define a central bore 41. It is contemplated that each sleeve element 40 of the plurality of sleeve elements can be configured for selective, removable engagement with adjacent sleeve elements of the plurality of sleeve elements.

In another aspect, as shown in FIGS. 1 and 3, the plurality of sleeve elements 40 can optionally comprise at least one intermediate sleeve element 40$b$ configured for positioning between the proximal and distal sleeve elements 40$a$, 40$c$ relative to the common longitudinal axis 12 of the abutment system 10. In an additional aspect, each sleeve element 40 of the plurality of sleeve elements can have a proximal portion 42 and a distal portion 46. In this aspect, the proximal portion 42$a$, 42$b$, 42$c$ of each sleeve element 40$a$, 40$b$, 40$c$ can have inner and outer surfaces 43$a$, 43$b$, 43$c$, 44$a$, 44$b$, 44$c$, while the distal portion 46$a$, 46$b$, 46$c$ of each sleeve element 40$a$, 40$b$, 40$c$ can have inner and outer surfaces 47$a$, 47$b$, 47$c$. It is contemplated that the inner surfaces 43$a$, 43$b$, 43$c$, 47$a$, 47$b$, 47$c$ of the proximal and distal portions 42$a$, 42$b$, 42$c$, 46$a$, 46$b$, 46$c$ of each sleeve element 40$a$, 40$b$, 40$c$ can cooperate to define the central bore 41$a$, 41$b$, 41$c$ of the sleeve element.

Figure 8A:
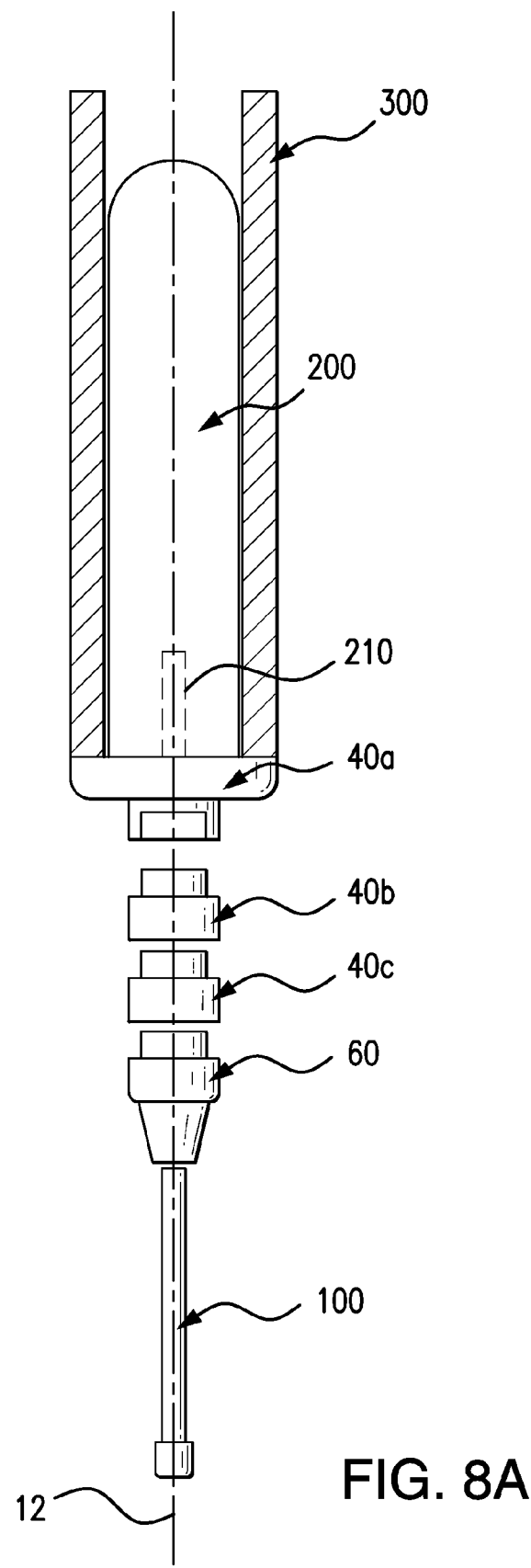
FIG. 8A is an exploded view of an exemplary abutment system as disclosed herein, prior to attachment of the abutment system to an exemplary implant stem.
Figure 8B:
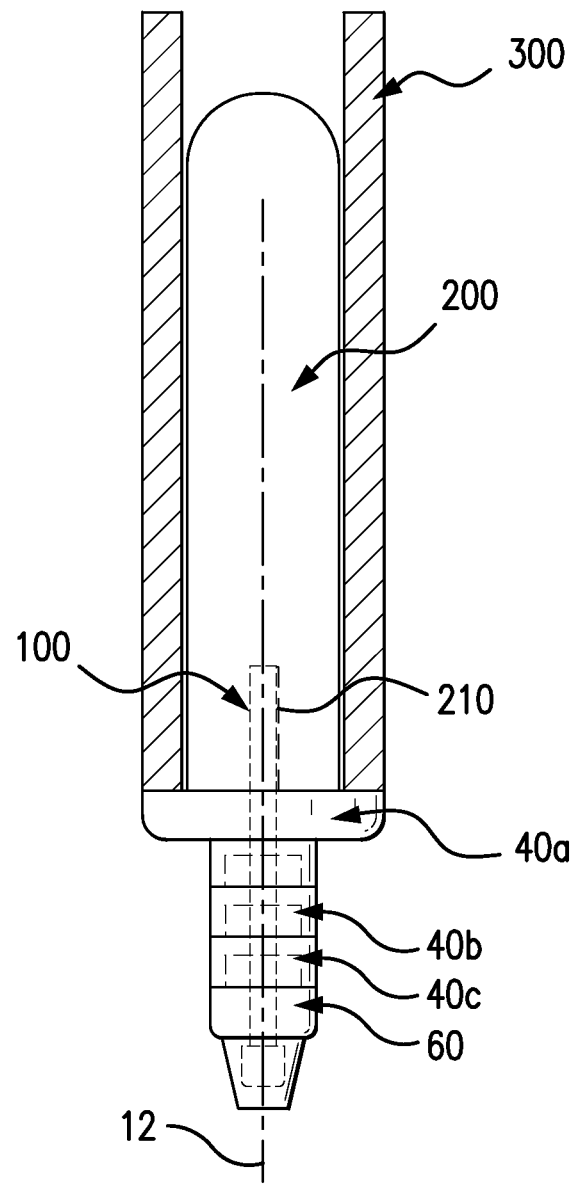
FIG. 8B depicts the abutment system of FIG. 8A, following attachment of the abutment system to the implant stem.

Optionally, in some aspects, as shown in FIG. 8, the central bores 41$a$, 41$b$, 41$c$ of the interlocking sleeve elements 40$a$, 40$b$, 40$c$ can be configured to receive a fixation bolt 100. In these aspects, it is contemplated that the proximal sleeve element 40$a$ can optionally be configured for contact with the implant stem 200 and/or soft tissue adjacent to a distal portion of the implant stem. It is further contemplated that the implant stem 200 to which the abutment system 10 is operatively coupled can define a cavity 210 configured to receive a proximal portion of the fixation bolt 100. It is further contemplated that the fixation bolt 100 can be configured for threaded engagement with the implant stem 200 within the cavity 210. Thus, following receipt of the fixation bolt 100 within the central bores 41$a$, 41$b$, 41$c$ of the interlocking sleeve elements 40$a$, 40$b$, 40$c$ and engagement between the fixation bolt and the implant stem 200, the proximal sleeve element 40$a$ can be bone-anchored.

Optionally, in other exemplary aspects, the abutment system 10 can comprise a base element 20. In these aspects, the base element 20 can be operatively secured to the implant stem 200, and the plurality of interlocking sleeve elements 40 and the end cap 60 can be operatively coupled to the base element. Thus, it is contemplated that the base element 20 can be bone-anchored.

In one aspect, and with reference to FIGS. 1-2, the base element 20 of the abutment system 10 can have a flange 22. It is contemplated that the flange can define a central bore configured to receive the fixation bolt 100. Alternatively, in another aspect, the base element can have an elongate shaft 24. In this aspect, the flange 22 can have a first surface 26, an opposed second surface 28, and an outer edge 30 extending between the first and second surfaces. It is contemplated that the flange 22 can have an outer radius 23 ranging from about 15 mm to about 20 mm. In some aspects, the outer radius 23 can be about 17.5 mm. It is further contemplated that the elongate shaft 24 can have an outer radius 25 ranging from about 1 mm to about 5 mm. In some aspects, the outer radius 25 can be about 2.5 mm. In another aspect, it is contemplated that the first surface 26 of the flange 22 can define a proximal end 21 of the base element 20. In this aspect, the proximal end 21 of the base element 20 can be configured for operative coupling to the implant stem 200. For example, it is contemplated that the proximal end 21 of the base element 20 can define at least one engagement element (such as, for example and without limitation, a threaded extension portion, not shown) configured for engagement with a selected portion of the implant stem 200 (such as, for example and without limitation, cavity 210, as shown in FIG. 8). In an additional aspect, the elongate shaft 24 can extend from a central portion 32 of the flange 22 away from the proximal end 21 of the base element 20 relative to the common longitudinal axis 12 of the abutment system 10.

In exemplary aspects, it is contemplated that the flange 22 can have a longitudinal length 34 ranging from about 5 mm to about 10 mm. In some aspects, the longitudinal length 34 can be about 7 mm. It is contemplated that the outer edge 30 of the flange can have a longitudinal length 36 ranging from about 1 mm to about 5 mm. In some aspects, the longitudinal length 36 can be about 3 mm. It is further contemplated that the elongate shaft 24 can have a longitudinal length 38 ranging from about 20 mm to about 30 mm. In some aspects, the longitudinal length 38 can be about 25 mm. In another exemplary aspect, it is contemplated that the second surface 28 of the flange 22 can be sloped radially inwardly toward the common longitudinal axis 12 at an angle 29, as measured from a plane positioned perpendicular to the common longitudinal axis 12.

Optionally, in other exemplary aspects, and with reference to FIGS. 1-5, each central bore 41a, 41b, 41c of the plurality of interlocking sleeve elements 40a, 40b, 40c can be configured to receive the elongate shaft 24 of the base element 20. In these aspects, the proximal sleeve element 40a of the plurality of sleeve elements can be configured for engagement with the flange 22 of the base element 20.

In exemplary aspects, the inner surface 43a of the proximal portion 42a of the proximal sleeve element 40a can optionally define a cavity 45 configured to receive the flange 22 of the base element 20. In these aspects, it is contemplated that the outer edge 30 of the flange 22 of the base element 20 can be configured for threaded engagement with the inner surface 43a of the proximal portion 42a of the proximal sleeve element 40a. In another aspect, it is contemplated that the outer surface 48a of the distal portion 46a of the proximal sleeve element 40a can be sloped radially inwardly toward the common longitudinal axis 12 at an angle 50, as measured relative to a plane positioned perpendicular to the common longitudinal axis 12, moving away from the proximal portion 42a of the proximal sleeve element. In this aspect, the inner surface 47a of the distal portion 46a of the proximal sleeve can be sloped radially inwardly toward the common longitudinal axis 12 at an angle that is less than angle 50 by angle 51. It is contemplated that angle 50 can range from about 25 degrees to about 30 degrees, while the angle 51 can range from about 5 degrees to about 10 degrees. Thus, it is contemplated that the inner surface 47a of the distal portion 46a of the proximal sleeve can be sloped radially inwardly toward the common longitudinal axis 12 at an angle ranging from about 15 degrees to about 25 degrees. In a further aspect, as shown in FIGS. 1 and 3, it is contemplated that the proximal sleeve element 40a can comprise a lip 52 circumferentially surrounding the central bore 41a of the proximal sleeve element. In this aspect, the lip 52 can protrude from the outer surface 48a of the distal portion 46a relative to the common longitudinal axis 12 of the abutment system 10. It is contemplated that the lip 52 can have a longitudinal length 53 ranging from about 2 mm to about 7 mm. In some aspects, the longitudinal length 53 can be about 4.5 mm. Optionally, the lip 52 can have an inner surface 54 that defines a seat for the proximal portion 42a of the proximal sleeve element 40a. In another aspect, the lip 52 can have an inner diameter 59.

Figure 5A:
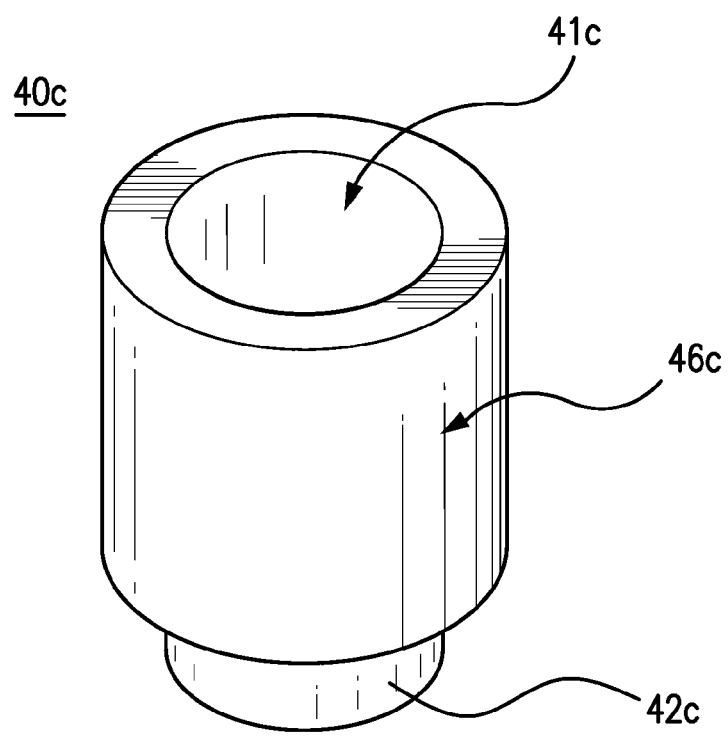
FIG. 5A depicts a perspective view of the distal sleeve element.
Figure 5B:
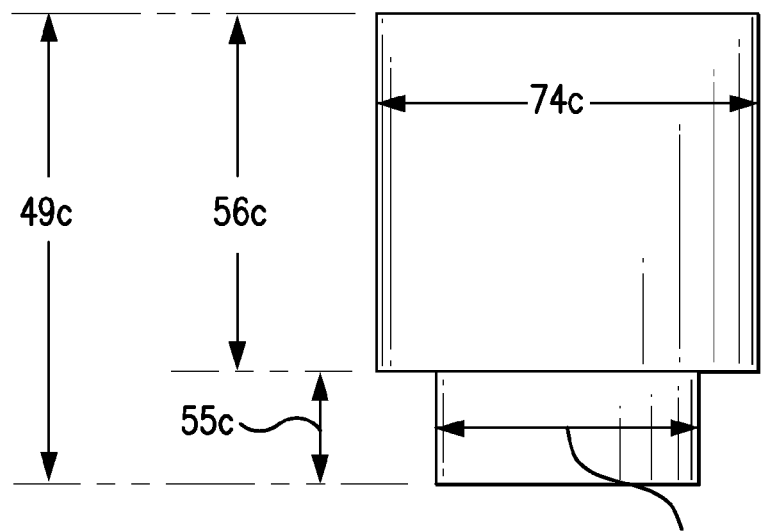
FIG. 5B depicts a side view of the distal sleeve element.
Figure 5C:
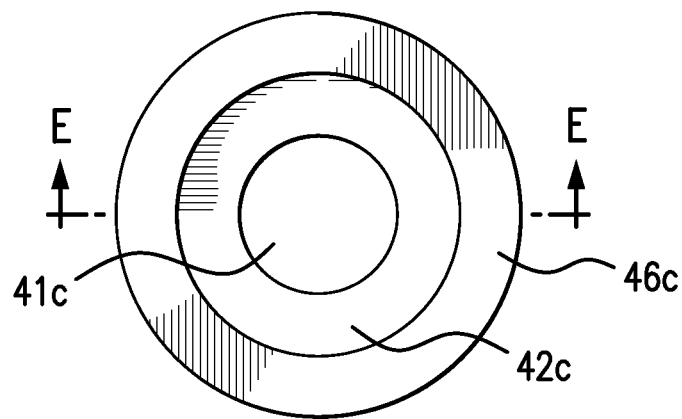
FIG. 5C depicts a top view of the distal sleeve element.
Figure 5D:
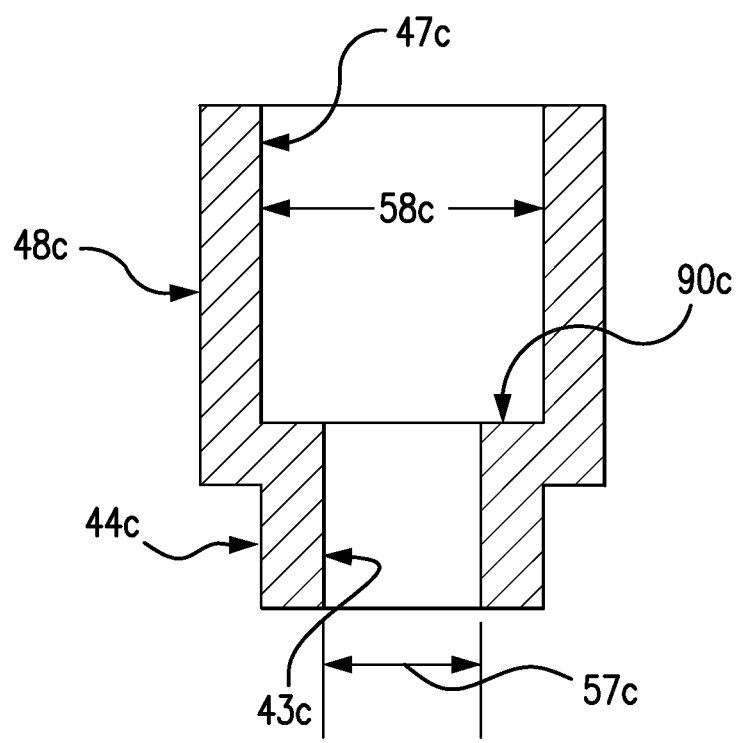
FIG. 5D depicts a cross-sectional view of the distal sleeve element of FIG. 5C, taken at line E-E.
Figure 6A:
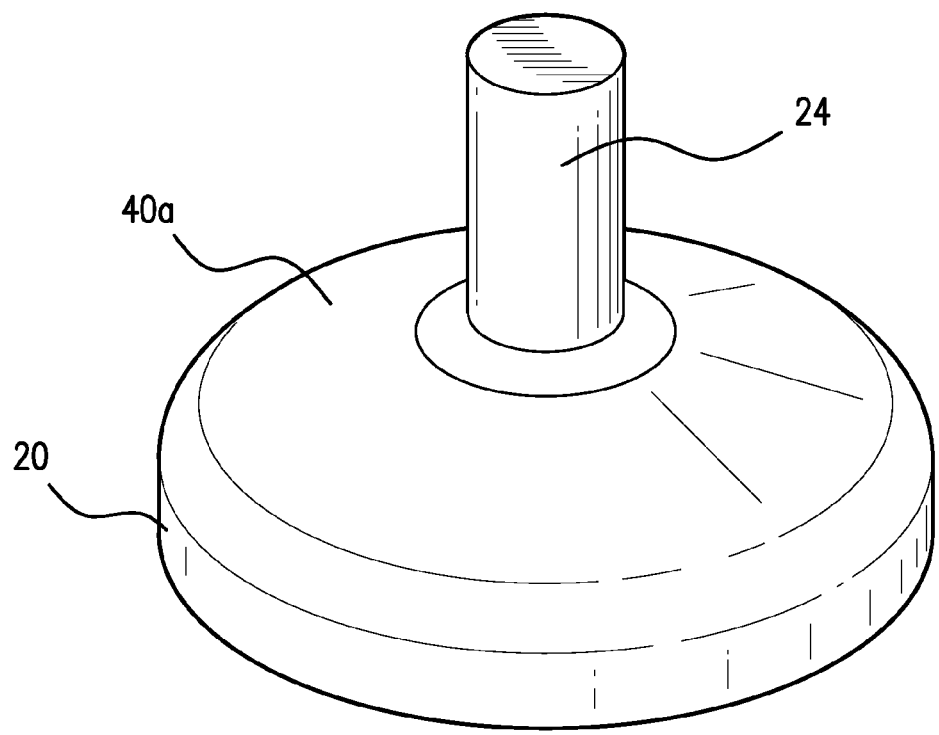
FIG. 6A depicts a perspective view of the base element and the proximal sleeve element.
Figure 6B:
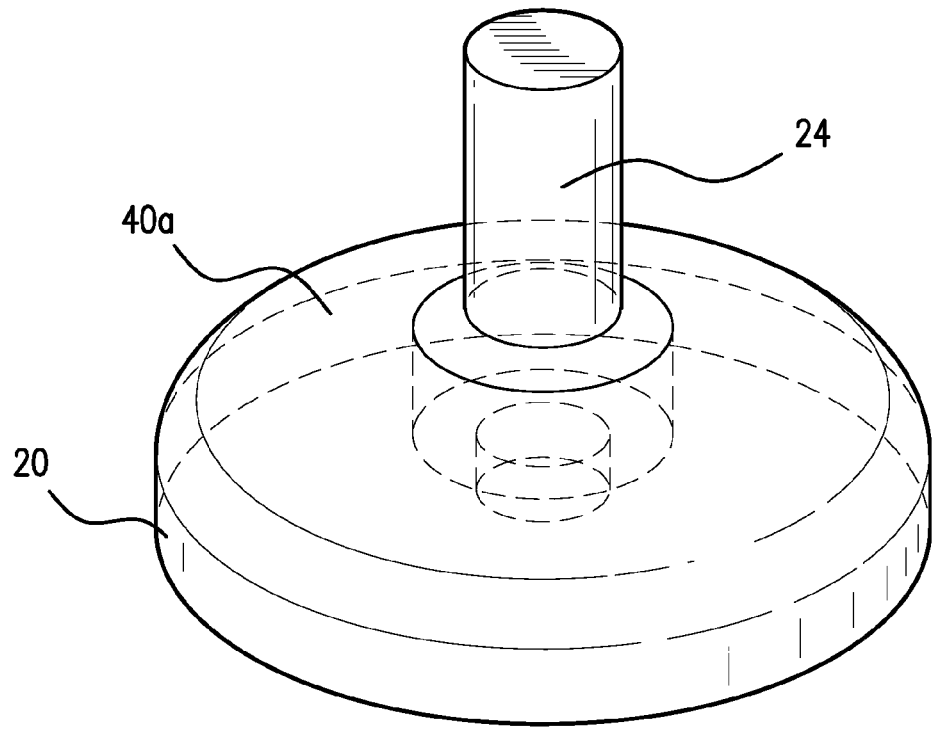
FIG. 6B depicts a transparent perspective view of the base element and the proximal sleeve element.
Figure 6C:
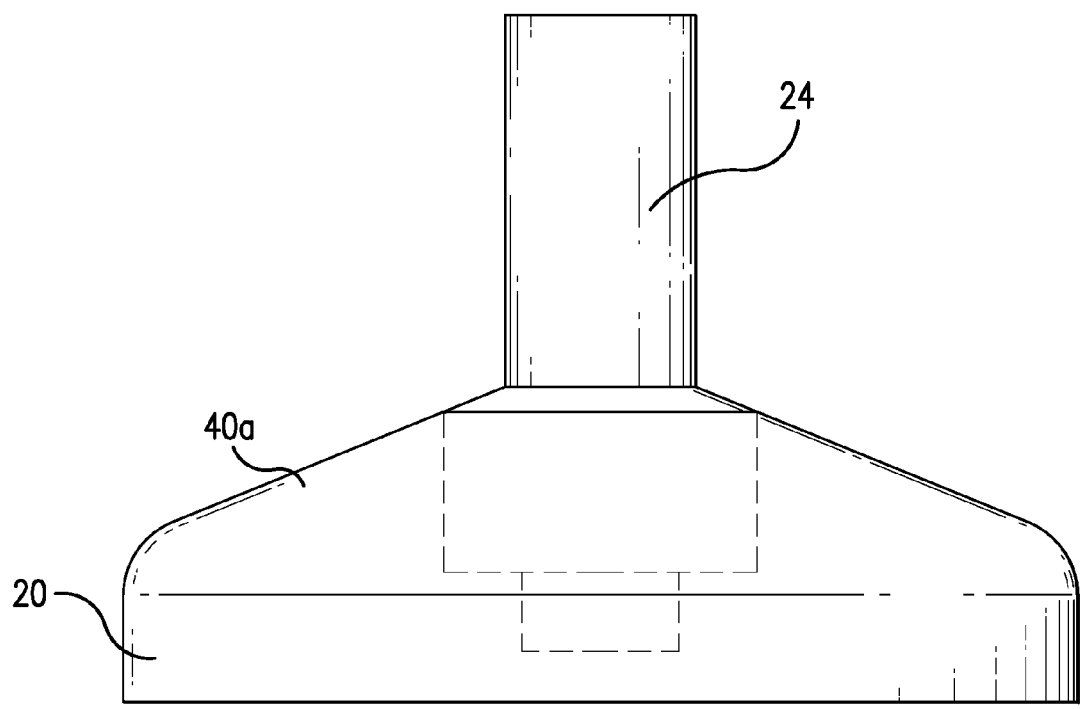
FIG. 6C depicts a transparent side view of the base element and the proximal sleeve element.

In additional exemplary aspects, and with reference to FIG. 4, the outer surface 44b of the proximal portion 42b of the at least one intermediate sleeve element 40b can be configured for receipt within the central bore 41 of an adjacent sleeve element and configured for removable engagement with the inner surface 47 of the distal portion 46 of the adjacent sleeve element. In these aspects, the outer surface 44 of the proximal portion 42 of each sleeve element 40 can be further configured for receipt within the central bore 41 of an adjacent sleeve element of the plurality of sleeve elements and configured for removable engagement with the inner surface 47 of the distal portion 46 of the adjacent sleeve element. It is contemplated that the outer surface 44 of the proximal portion 42 of each intermediate sleeve element 40b can be configured for threaded engagement with the inner surface 47 of the distal portion 46 of an adjacent sleeve element of the plurality of sleeve elements. As shown in FIGS. 4D and 5D, it is further contemplated that the inner surface 47b, 47c of the distal portion 46b, 46c of a sleeve element 40b, 40c can define a seat 90b, 90c for the proximal portion 42 of an adjacent sleeve element.

In additional exemplary aspects, the proximal portion 42a, 42b, 42c of each sleeve element 40a, 40b, 40c can have a longitudinal length 55a, 55b, 55c (for example and without limitation, ranging from about 2 mm to about 6 mm), while the distal portion 46a, 46b, 46c of each sleeve element can have a longitudinal length 56a, 56b, 56c (for example and without limitation, ranging from about 4 mm to about 8 mm for the proximal sleeve element 40a, from about 6 mm to about 12 mm for the intermediate sleeve element 40b, and from about 10 mm to about 15 mm for the distal sleeve element 40c). In additional aspects, the proximal portion 42a, 42b, 42c of each sleeve element 40a, 40b, 40c can have an inner diameter 57a, 57b, 57c (for example and without limitation, ranging from about 20 mm to about 40 mm for the proximal sleeve element 40a, from about 2 mm to about 8 mm for the intermediate sleeve element 40b, and from about 2 mm to about 8 mm for the distal sleeve element 40c) and an outer diameter 72a, 72b, 72c (for example and without limitation, ranging from about 5 mm to about 15 mm for the intermediate sleeve element 40b and the distal sleeve element 40c). In further aspects, the distal portion 46a, 46b, 46c of each sleeve element 40 can have an inner diameter 58a, 58b, 58c (for example and without limitation, ranging from about 5 mm to about 15 mm for the intermediate sleeve element 40b and the distal sleeve element 40c) and an outer diameter 74a, 74b, 74c (for example and without limitation, ranging from about 10 mm to about 15 mm for the intermediate sleeve element 40b and the distal sleeve element 40c).

In further exemplary aspects, the outer surface 48 of the distal portion 46 of at least one sleeve element 40 of the plurality of sleeve elements can comprise a porous material. In additional exemplary aspects, it is contemplated that at least a portion of the outer surface 48 of the distal portion 46 of each sleeve element 40 of the plurality of sleeve elements can comprise a porous material. It is contemplated that the porous material of the outer surface(s) 48 of the distal portion(s) 46 of the sleeve element(s) 40 can comprise any metal, polymer, or ceramic material having a desired porosity. In exemplary aspects, the porous material can be porous titanium. In other exemplary aspects, the desired porosity of the outer surface 48 of the distal portion 46 of a particular sleeve element 40 can range from about 40% to about 70%. In these aspects, it is contemplated that the size of each pore of the outer surface 48 of the distal portion 46 of the sleeve element 40 can range from about 25 μm to about 1,000 μm. In some aspects, it is contemplated that the size of each pore of the outer surface 48 of the distal portion 46 of the sleeve element 40 can range from about 30 μm to about 400 μm.

In still further exemplary aspects, the outer surface 48 of the distal portion 46 of at least one sleeve element 40 of the plurality of sleeve elements can be configured to inhibit bio-adhesion. Optionally, the portion of the outer surface 48 of the distal portion 46 of the at least one sleeve element 40 that is configured to inhibit bio-adhesion can be an ultra-low friction surface as defined above. Alternatively, the portion of the outer surface 48 of the distal portion 46 of the at least one sleeve element 40 that is configured to inhibit bio-adhesion can be a highly polished surface.

In exemplary aspects, it is contemplated that the highly polished surfaces described herein can have $R_t$, or maximal peak to valley (P-V), values from profilometry and/or white light interferometry analysis that are less than about 20 μm. In some aspects, the highly polished surfaces described herein can have $R_t$, or maximal peak to valley (P-V), values from profilometry and/or white light interferometry analysis that are less than about 10 μm. In other aspects, the highly polished surfaces described herein can have $R_t$, or maximal peak to valley (P-V), values from profilometry and/or white light interferometry analysis that are less than about 6 μm. In further exemplary aspects, the highly polished surfaces described herein can have $R_t$, or maximal peak to valley (P-V), values from profilometry and/or white light interferometry analysis that are less than about 4 μm. It is further contemplated that these values can be pre-determined, or designed for, by an appropriate combination of milling bit coating and/or surface coating. Suitable profilometry analyses can be conducted by sweeping and/or sliding a probe having a specific geometry over the surface to determine the relative roughness of the surface material. White light interferometry, an optical technique, can be employed to use light refraction and optics (and/or physics) to determine the relative roughness of a given surface material. It is contemplated that both profilometry and interferometry, as well as other known comparable techniques, can be used in conjunction with one another to characterize the surfaces of the various elements of the disclosed implant system. Optionally, in exemplary aspects, it is contemplated that the ultra-low friction surfaces described herein can have $R_t$, or maximal peak to valley (P-V), values from profilometry and/or white light interferometry analysis that are less than about 20 μm. In some aspects, the ultra-low friction surfaces described herein can have $R_t$, or maximal peak to valley (P-V), values from profilometry and/or white light interferometry analysis that are less than about 5 μm. In other aspects, the ultra-low friction surfaces described herein can have $R_t$, or maximal peak to valley (P-V), values from profilometry and/or white light interferometry analysis that are less than about 3 μm. In further exemplary aspects, the ultra-low friction surfaces described herein can have $R_t$, or maximal peak to valley (P-V), values from profilometry and/or white light interferometry analysis that are less than about 2 μm.

In an additional aspect, the outer surface(s) 48 of the distal portion(s) 46 of one or more of the sleeve elements 40 can be coated with at least one of a biomimetic coating or a soft tissue-integration-promoting compound. In this aspect, it is contemplated that the biomimetic coating(s) and/or soft-tissue-integration-promoting compounds can comprise one or more integrin-recognizing polymers or protein complexes with advantageous bioactive capacities that promote soft tissue integration and limit soft tissue regression.

In another exemplary aspect, the outer surface 48a of the distal portion 46a of the proximal sleeve element 40a can comprise a first material, and the outer surface 48 of the distal portion 46 of at least one other sleeve element 40 of the plurality of sleeve elements can comprise a second material that is different from the first material.

In another aspect, and with reference to FIG. 1, the end cap 60 of the abutment system 10 can be configured for engagement with the distal sleeve element 40c of the plurality of sleeve elements. In this aspect, it is contemplated that the end cap 60 can have an outer surface 62, a proximal portion 66 and a distal portion 68. It is further contemplated that the distal portion 68 of the end cap can define a distal end 64 of the end cap 60 configured for attachment to an exo-prosthesis.

In one optional aspect, and with reference to FIG. 8, when the abutment system 10 does not comprise a base element 20, it is contemplated that the end cap 60 of the abutment system 10 can define a central bore configured to receive the fixation bolt 100. In this aspect, it is further contemplated that the end cap 60 can define a seat within the central bore of the end cap for supporting a head of the fixation bolt 100. It is still further contemplated that, upon operative coupling between the end cap 60 and the plurality of sleeve elements 40, the central bores 41 of the sleeve elements can be substantially axially aligned with the central bore of the end cap.

Optionally, in another alternative aspect, when the abutment system comprises a base element 20, it is contemplated that the end cap 60 of the abutment system 10 can define a cavity configured to receive a distal portion of the elongate portion 24 of the base element.

In one exemplary aspect, the at least one intermediate sleeve element can comprise a single intermediate sleeve element 40b. In this aspect, the outer surface 44b of the proximal portion 42b of the intermediate sleeve element 40b can be configured for threaded engagement with the inner surface 47b of the distal portion 46a of the proximal sleeve element 40a. It is contemplated that the outer surface 44c of the proximal portion 42c of the distal sleeve element 40c can be configured for threaded engagement with the inner surface 48b of the distal portion 46b of the intermediate sleeve element 40b. It is further contemplated that the inner surface 47c of the distal portion 46c of the distal sleeve element 40c can be configured for threaded engagement with the outer surface 62 of the proximal portion 66 of the end cap 60.

In another exemplary aspect, and with reference to FIGS. 1 and 4-5, it is contemplated that the distal portions 46a, 46b, 46c of the proximal, intermediate, and distal sleeve elements 40a, 40b, 40c can have respective longitudinal lengths 49a, 49b, 49c. In this aspect, it is contemplated that the longitudinal length 49b of the distal portion 46b of the intermediate sleeve element 40b can be less than the longitudinal length 49c of the distal portion 46c of the distal sleeve element 40c.

In exemplary aspects, the longitudinal length 49a of the proximal sleeve element 40a can range from about 10 mm to about 20 mm. In some aspects, the longitudinal length 49a of the proximal sleeve element 40a can be about 15 mm. It is contemplated that the longitudinal length 49b of the intermediate sleeve element 40b can range from about 10 mm to about 15 mm. In some aspects, the longitudinal length 49b of the intermediate sleeve element 40b can be about 12.5 mm. It is further contemplated that the longitudinal length 49c of the distal sleeve element 40c can range from about 10 mm to about 20 mm. In some aspects, the longitudinal length 49c of the distal sleeve element 40c can be about 16.5 mm.

Optionally, in one aspect, the end cap 60 can comprise an exo-prosthetic docking portion 70 positioned between the proximal and distal portions 66, 68 of the end cap relative to the common longitudinal axis 12 of the abutment system 10. In this aspect, it is contemplated that, upon threaded engagement between the outer surface 62 of the proximal portion 66 of the end cap 60 and the inner surface 47c of the distal portion 46c of the distal sleeve element 40c, the exo-prosthetic docking portion 70 of the end cap can be substantially flush with the outer surface 48c of the distal portion of the distal sleeve element. As shown in FIG. 2, it is further contemplated that the exo-prosthetic docking portion 70 can extend outwardly from the outer surface 62 of the end cap 60. Optionally, in a further aspect, it is contemplated that, following engagement between the intermediate sleeve element 40b and the distal sleeve element 40c, the outer surfaces 48b, 48c of the distal portions 46b, 46c of the intermediate and distal sleeve elements can be substantially flush to one another.

Alternative Configurations of the Abutment System

In one optional, exemplary aspect, it is contemplated that the base element 20 can be integrally formed with an implant, such as, for example and without limitation, an OI implant as described herein. In this aspect, it is contemplated that the proximal end 21 of the base element 20 can be integrally and contiguously formed with a distal end of an implant such that the elongate shaft 24 of the base element 20 extends distally relative to the distal end of the implant. Thus, it is contemplated that a proximal/insertional portion of the implant can be configured for osseo-integrative engagement with a selected bone of the subject while a distal portion of the implant can comprise a base element as described herein.

Figure 7A:
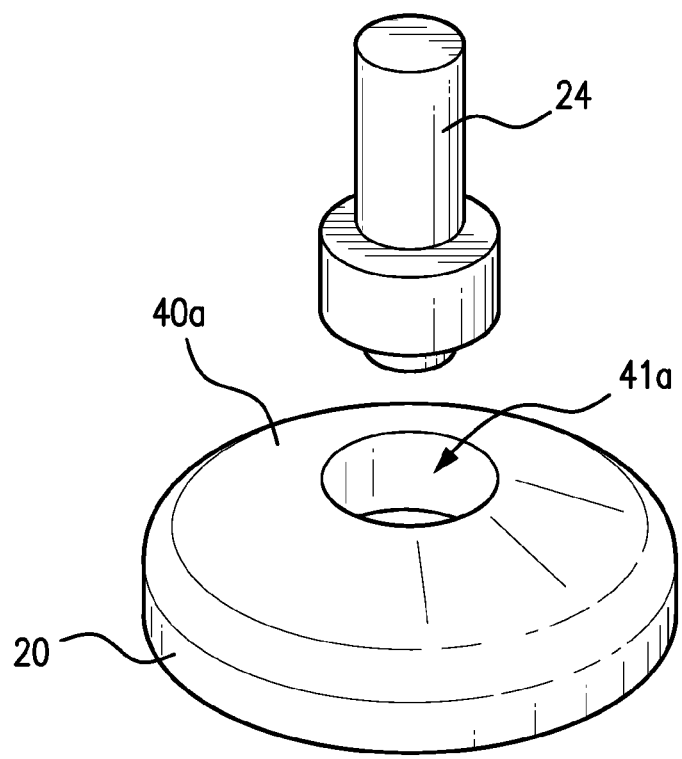
FIG. 7A depicts an exploded perspective view of the base element and the proximal sleeve element.
Figure 7B:
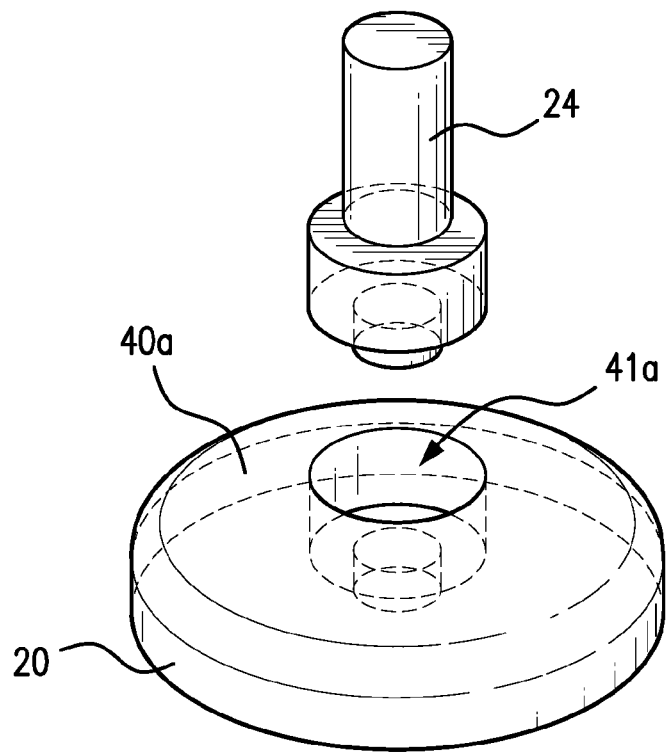
FIG. 7B depicts an exploded transparent perspective view of the base element and the proximal sleeve element.

With reference to FIGS. 6A-7C, in another optional, exemplary aspect, it is contemplated that the elongate shaft 24 of the base element 20 can be configured for selective, removable engagement with the flange 22 of the base element. For example, in one aspect, the elongate shaft 24 can be configured for selective, secure attachment to the central portion 32 of the flange 22. In this aspect, it is contemplated that the central portion 32 of the flange 22 can define a cavity configured to receive a proximal portion of the elongate shaft 20. In another aspect, as shown in FIG. 7C, it is contemplated that the elongate shaft 24 can comprise a proximal portion 84, a distal portion 80, and an intermediate portion 82 positioned between the proximal and distal portions. It is further contemplated that the proximal, distal, and intermediate portions 84, 80, 82 can have respective diameters, with the diameter of the intermediate portion being greater than the diameters of the proximal and distal portions. In exemplary aspects, it is contemplated that the diameter of the proximal portion 84 can range from about 3 mm to about 10 mm. In other aspects, it is contemplated that the diameter of the proximal portion 84 can be about 4 mm. After the elongate shaft 24 is secured to the flange 22 of the base element 20, the proximal sleeve element 40a can be secured to the flange. It is contemplated that the diameter of the intermediate portion 82 of the elongate shaft 24 can be less than the inner diameter of the central bore of the proximal sleeve element 41a such that the intermediate portion of the elongate shaft can be received within the central bore of the proximal sleeve element while the proximal sleeve element is engaged with the base element 20. As shown in FIG. 7C, it is still further contemplated that the intermediate portion 82 of the elongate shaft 24 can have a sloped portion 86 positioned at a distal end of the proximal sleeve element when the elongate shaft is secured to the flange 22 of the base element 20. In exemplary aspects, the sloped portion 86 of the elongate shaft 24 can have a slope substantially matching the slope of the outer surface 48a of the distal portion 46a of the proximal sleeve element, thereby forming a substantially contiguous sloped surface (See FIGS. 6A-6C).

In additional, optional aspects, it is contemplated that the base element 20 and the proximal sleeve element 40a can be integrally formed as a single component.

In further optional aspects, it is contemplated that the elongate shaft 24 of the base element can be eliminated. In these aspects, it is contemplated that the proximal sleeve element 40a can be configured for direct engagement with the flange 22 of the base element 20, with the remaining sleeve elements 40b, 40c configured for direct engagement with adjacent sleeve elements such that the sleeve elements cooperate to define a single, solid modular component.

Kits Containing One or More Components of the Abutment System

In various aspects, it is contemplated that the abutment system 10 and components thereof can be provided in a kit. In these aspects, it is contemplated that the kit can comprise a first set of sleeve elements as described herein, as well as a set of replacement sleeve elements that are configured for interchangeable use with and replacement of one or more sleeve elements of the first set of sleeve elements. It is further contemplated that the replacement sleeve elements can comprise different materials and/or have different material properties than at least one sleeve element of the first set of sleeve elements. It is still further contemplated that the respective components of the abutment system described herein can comprise labelling, color-coding, or other indicia of the particular sizing and/or material characteristics of the component that enable a surgeon or other medical practitioner to determine whether the component is appropriate for use in a particular procedure and/or whether the component is complementary in size and/or function to other components of the abutment system.

Use of the Abutment System

In use, the disclosed abutment system can be used in a method of operatively coupling an implant stem to a prosthesis, such as, for example, an exo-prosthesis. In exemplary aspects, the implant stem can be an OI implant stem. In one aspect, the method can comprise positioning the implant stem within a prepared site of a selected tissue region of a subject, such as, for example, a selected bone 300 (See FIG. 8). In another aspect, the method can comprise operatively coupling the abutment system to the implant stem. In this aspect, the step of operatively coupling the abutment system to the implant stem can comprise operatively coupling the proximal sleeve element of the plurality of sleeve elements to the implant stem. It is contemplated that the step of operatively coupling the abutment system to the implant stem can further comprise positioning each sleeve element of the plurality of sleeve elements in selective, removable engagement with adjacent sleeve elements of the plurality of sleeve elements. In a further aspect, the method can comprise positioning the end cap of the abutment system in engagement with the distal sleeve element of the plurality of sleeve elements. In still another aspect, the method can comprise securing the prosthesis to the abutment system.

Optionally, in additional aspects, the method of operatively coupling the implant stem to the exo-prosthesis can further comprise selectively removing at least one sleeve element of the plurality of sleeve elements. In these aspects, the method can optionally further comprise selectively replacing at least one original sleeve element of the plurality of sleeve elements with a corresponding substitute sleeve element.

In some exemplary aspects, the step of operatively coupling the abutment system to the implant stem can comprise positioning the fixation bolt through the central bores of the plurality of sleeve elements, end cap, and/or base element and into the cavity defined within the implant stem. In these aspects, the step of operatively coupling the abutment system to the implant stem can further comprising threadingly engaging a proximal portion of the fixation bolt with the implant stem within the cavity of the implant stem.

In other exemplary aspects, it is contemplated that the step of operatively coupling the abutment system to the implant stem can comprise operatively coupling the proximal end of the base element of the abutment system to the implant stem (i.e., an endo-prosthesis). However, as set forth herein, it is understood that, in alternative aspects, the base element can optionally be integrally formed with the implant stem. Optionally, in some aspects, when the elongate shaft of the base element is selectively detachable from the flange of the base element as set forth herein, the method can comprise securing the elongate shaft of the base element to the flange of the base element. In an additional aspect, the method can comprise operatively positioning the plurality of interlocking sleeve elements of the abutment system thereon the elongate shaft of the base element. In this aspect, the proximal sleeve element of the plurality of sleeve elements can be positioned in engagement with the flange of the base element, and each sleeve element of the plurality of sleeve elements can be positioned in selective, removable engagement with adjacent sleeve elements of the plurality of sleeve elements.

It is contemplated that the various components of the abutment system 10 can comprise conventional surgical-quality metallic materials, including, for example and without limitation, titanium, cobalt chrome, and the like. It is further contemplated that the porosity or biomimetic surface coating of the abutment system 10 can improve soft-tissue outcomes by reducing relative motion between the abutment system 10 and the surrounding soft tissue to decrease the inflammatory response of the subject and to reduce or prevent infection through the promotion of soft-tissue capture, which helps maintain a biological barrier to the external environment.

Upon secure receipt of the implant stem within the prepared site, it is contemplated that the porous material and/or biomimetic coating(s) of the various components of the abutment system 10 can promote formation of a seal between the skin of the subject and the implant stem, thereby reducing the likelihood of infection in the subject and minimizing the possibility of formation of a pocket (or sinus tract) between the skin of the subject and the implant stem.

It is contemplated that the abutment system described herein can be configured for operative securement to any conventional implant stem and any conventional exo-prosthesis.

It should be appreciated that the angles and dimensions depicted in the Figures may be exaggerated for clarity and, consequently, may not be to scale.

In exemplary aspects, an abutment system for operatively coupling an implant stem to an exo-prosthesis is provided, the implant stem configured for positioning within a prepared site of a selected bone and surrounding soft tissue of a subject, the abutment system having a common longitudinal axis, the abutment system comprising: a plurality of interlocking sleeve elements, the plurality of sleeve elements comprising a proximal sleeve element and a distal sleeve element, the proximal sleeve element of the plurality of sleeve elements being configured for operative coupling to the implant stem, each sleeve element of the plurality of sleeve elements configured for selective, removable engagement with adjacent sleeve elements of the plurality of sleeve elements; and an end cap configured for engagement with the distal sleeve element of the plurality of sleeve elements, the end cap having a proximal portion and a distal portion, the distal portion of the end cap defining a distal end of the end cap, the distal end of the end cap being configured for engagement with the exo-prosthesis.

In these aspects, the abutment system can optionally comprise a base element configured for operative coupling to the implant stem, wherein the proximal sleeve element of the plurality of interlocking sleeve elements is configured for engagement with the base element.

In further exemplary aspects, an abutment system for operatively coupling an implant stem to an exo-prosthesis is provided, the implant stem being configured for positioning within a prepared site of a selected bone and surrounding soft tissue of a subject, the abutment system having a common longitudinal axis, the abutment system comprising: a base element having a flange and an elongate shaft, the flange having a first surface, an opposed second surface, and an outer edge extending between the first and second surfaces, the first surface of the flange defining a proximal end of the base element, the proximal end of the base element configured for operative coupling to the implant stem, the elongate shaft extending from a central portion of the flange away from the proximal end of the base element relative to the common longitudinal axis of the abutment system; a plurality of interlocking sleeve elements, each sleeve element of the plurality of sleeve elements defining a central bore configured for receipt of the elongate shaft of the base element, the plurality of sleeve elements comprising a proximal sleeve element and a distal sleeve element, the proximal sleeve element of the plurality of sleeve elements being configured for engagement with the flange of the base element, each sleeve element of the plurality of sleeve elements configured for selective, removable engagement with adjacent sleeve elements of the plurality of sleeve elements; and an end cap configured for engagement with the distal sleeve element of the plurality of sleeve elements, the end cap having a proximal portion and a distal portion, the proximal and distal portions of the end cap having respective outer surfaces, the distal portion of the end cap defining a distal end of the end cap, the distal end of the end cap being configured for engagement with the exo-prosthesis.

In another exemplary aspect, the plurality of sleeve elements comprise at least one intermediate sleeve element configured for positioning between the proximal and distal sleeve elements relative to the common longitudinal axis of the abutment system.

In another exemplary aspect, each sleeve element of the plurality of sleeve elements has a proximal portion and a distal portion, wherein the proximal and distal portions of each sleeve element have respective inner and outer surfaces and the inner surfaces of the proximal and distal portions of each sleeve element cooperate to define the central bore of the sleeve element.

In another exemplary aspect, the inner surface of the proximal portion of the proximal sleeve element defines a cavity configured to receive the flange of the base element.

In another exemplary aspect, the outer edge of the flange of the base element is configured for threaded engagement with the inner surface of the proximal portion of the proximal sleeve element.

In another exemplary aspect, the outer surface of the proximal portion of the at least one intermediate sleeve element is configured for receipt within the central bore of an adjacent sleeve element and configured for removable engagement with the inner surface of the distal portion of the adjacent sleeve element, wherein the outer surface of the proximal portion of each sleeve element is further configured for receipt within the central bore of an adjacent sleeve element of the plurality of sleeve elements and for removable engagement with the inner surface of the distal portion of the adjacent sleeve element.

In another exemplary aspect, the outer surface of the proximal portion of each intermediate sleeve element is configured for threaded engagement with the inner surface of the distal portion of an adjacent sleeve element of the plurality of sleeve elements.

In another exemplary aspect, the outer surface of the distal portion of at least one sleeve element of the plurality of sleeve elements comprises a porous material.

In another exemplary aspect, the outer surface of the distal portion of at least one sleeve element of the plurality of sleeve elements is configured to inhibit bio-adhesion.

In another exemplary aspect, the outer surface of the distal portion of at least one sleeve element of the plurality of sleeve elements is configured to promote bio-adhesion and soft-tissue integration.

In another exemplary aspect, at least a portion of the outer surface of the distal portion of each sleeve element of the plurality of sleeve elements comprises a porous material.

In another exemplary aspect, the outer surface of the distal portion of the proximal sleeve element comprises a first material, wherein the outer surface of the distal portion of at least one other sleeve element of the plurality of sleeve elements comprises a material that is different from the first material.

In another exemplary aspect, the at least one intermediate sleeve element comprises a single intermediate sleeve element, the outer surface of the proximal portion of the intermediate sleeve element being configured for threaded engagement with the inner surface of the distal portion of the proximal sleeve element, wherein the outer surface of the proximal portion of the distal sleeve element is configured for threaded engagement with the inner surface of the distal portion of the intermediate sleeve element, and wherein the inner surface of the distal portion of the distal sleeve element is configured for threaded engagement with the outer surface of the proximal portion of the end cap.

In another exemplary aspect, the distal portions of the intermediate and distal sleeve elements have respective longitudinal lengths, wherein the longitudinal length of the distal portion of the intermediate sleeve element is less than the longitudinal length of the distal portion of the distal sleeve element.

In another exemplary aspect, the end cap comprises an exo-prosthesis docking portion positioned between the proximal and distal portions of the end cap relative to the common longitudinal axis of the abutment system, wherein, upon threaded engagement between the outer surface of the proximal portion of the end cap and the inner surface of the distal sleeve element, the exo-prosthesis docking portion of the end cap is substantially flush with the outer surface of the distal portion of the distal sleeve element.

In another exemplary aspect, following engagement between the intermediate sleeve element and the distal sleeve element, the outer surfaces of the distal portions of the intermediate and distal sleeve elements are substantially flush.

In another exemplary aspect, the outer surface of the distal portion of the proximal sleeve element is sloped inwardly relative to the common longitudinal axis of the abutment system moving away from the proximal portion of the proximal sleeve element.

In another exemplary aspect, the proximal sleeve element comprises a lip circumferentially surrounding the central bore of the distal portion of the proximal sleeve element and protruding from the outer surface of the distal end portion relative to the common longitudinal axis of the abutment system.

In another exemplary aspect, the elongate shaft of the base element is integrally formed with the flange of the base element.

In another exemplary aspect, the elongate shaft of the base element is configured for removable coupling to the flange of the base element.

In another exemplary aspect, a kit comprising the abutment system is provided.

In further exemplary aspects, a method of operatively coupling an implant stem to an exo-prosthesis is provided, comprising: positioning the implant stem within a prepared site of a selected bone and surrounding soft tissue of a subject; operatively coupling an abutment system to the implant stem, the abutment system having a common longitudinal axis and comprising a plurality of interlocking sleeve elements and an end cap, the plurality of interlocking sleeve elements comprising a proximal sleeve element and a distal sleeve element, wherein the proximal sleeve element is operatively coupled to the implant stem, and wherein each sleeve element of the plurality of sleeve elements is positioned in selective, removable engagement with adjacent sleeve elements of the plurality of sleeve elements; positioning the end cap of the abutment system in engagement with the distal sleeve element of the plurality of sleeve elements; and securing the exo-prosthesis to the abutment system.

In another exemplary aspect, the method further comprises selectively removing at least one sleeve element of the plurality of sleeve elements.

In another exemplary aspect, the method further comprises selectively replacing at least one original sleeve element of the plurality of sleeve elements with a corresponding substitute sleeve element.

In another exemplary aspect, the outer surface of the distal portion of the at least one original sleeve element comprises a first material, wherein the outer surface of the distal portion of the substitute sleeve element comprises a material that is different from the first material.

In another exemplary aspect, each sleeve element of the plurality of sleeve elements defines a central bore configured for receipt of a fixation bolt, wherein the implant stem defines a cavity configured to receive a proximal portion of the fixation bolt.

In still further exemplary aspects, a method of operatively coupling an implant stem to an exo-prosthesis is provided, comprising: positioning the implant stem within a prepared site of a selected bone and surrounding soft tissue of a subject; operatively coupling a proximal end of a base element of an abutment system to the implant stem, the abutment system having a common longitudinal axis, the base element having a flange and an elongate shaft, the flange having a first surface, an opposed second surface, and an outer edge extending between the first and second surfaces, the first surface of the flange defining the proximal end of the base element, the elongate shaft extending from a central portion of the flange away from the proximal end of the base element relative to the common longitudinal axis of the abutment system; operatively positioning a plurality of interlocking sleeve elements of the abutment system thereon the elongate shaft of the base element, each sleeve element of the plurality of sleeve elements defining a central bore configured for receipt of the elongate shaft of the base element, the plurality of sleeve elements comprising a proximal sleeve element and a distal sleeve element, the proximal sleeve element of the plurality of sleeve elements being positioned in engagement with the flange of the base element, each sleeve element of the plurality of sleeve elements being positioned in selective, removable engagement with adjacent sleeve elements of the plurality of sleeve elements; positioning an end cap of the abutment system in engagement with the distal sleeve element of the plurality of sleeve elements; and securing the exo-prosthesis to the abutment system.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. An abutment system configured to operatively couple an implant stem to a prosthesis positioned external to a selected bone of a subject, the implant stem configured for positioning within a prepared site of the selected bone and surrounding soft tissue of the subject, the abutment system having a common longitudinal axis, the abutment system comprising:

a base element having only one flange and an elongate shaft secured to the flange, the flange having a first surface, an opposed second surface, and an outer edge extending between the first and second surfaces, the first surface of the flange defining a proximal end of the base element, the proximal end of the base element configured for operative coupling to the implant stem, the elongate shaft extending from a central portion of the flange away from the base element in a distal direction relative to the common longitudinal axis of the abutment system;

a plurality of interlocking sleeve elements surrounding the elongate shaft of the base element, the plurality of interlocking sleeve elements configured to be positioned external to the bone but within the subject, each sleeve element of the plurality of sleeve elements defining a central bore that receives the elongate shaft of the base element, the plurality of sleeve elements comprising a proximal sleeve element and a distal sleeve element, wherein the proximal sleeve element engages the flange of the base element, each sleeve element of the plurality of sleeve elements being positioned in selective, removable engagement with adjacent sleeve elements of the plurality of sleeve elements, wherein the outer surface of the distal portion of at least one sleeve element of the plurality of sleeve elements is configured to promote soft-tissue integration;

and an end cap configured for engagement with the distal sleeve element of the plurality of sleeve elements, the end cap having a proximal portion and a distal portion, the proximal and distal portions of the end cap having respective outer surfaces, the distal portion of the end cap defining a distal end of the end cap, the distal end of the end cap being configured for engagement with the external prosthesis.

2. The abutment system of claim 1, wherein the plurality of sleeve elements comprises at least one intermediate sleeve element positioned between the proximal and distal sleeve elements relative to the common longitudinal axis of the abutment system.

3. The abutment system of claim 2, wherein each sleeve element of the plurality of sleeve elements has a proximal portion and a distal portion, wherein the proximal and distal portions of each sleeve element have respective inner and outer surfaces, and wherein the inner surfaces of the proximal and distal portions of each sleeve element cooperate to define the central bore of the sleeve element.

4. The abutment system of claim 3, wherein the inner surface of the proximal portion of the proximal sleeve element defines a cavity that receives the flange of the base element.

5. The abutment system of claim 4, wherein the outer edge of the flange of the base element is positioned in threaded engagement with the inner surface of the proximal portion of the proximal sleeve element.

6. The abutment system of claim 4, wherein the outer surface of the proximal portion of each intermediate sleeve element of the at least one intermediate sleeve element is received within the central bore of an adjacent sleeve element positioned proximally relative to the at least one intermediate sleeve element, wherein the adjacent sleeve element is selected from the group consisting of the proximal sleeve element and another intermediate sleeve element, and wherein the at least one intermediate sleeve element is positioned in removable engagement with the inner surface of the distal portion of the adjacent sleeve element.

7. The abutment system of claim 6, wherein the outer surface of the proximal portion of each intermediate sleeve element is positioned in threaded engagement with the inner surface of the distal portion of the adjacent sleeve elements.

8. The abutment system of claim 2, wherein the at least one intermediate sleeve element comprises a single intermediate sleeve element, the outer surface of the proximal portion of the intermediate sleeve element being positioned in threaded engagement with the inner surface of the distal portion of the proximal sleeve element, wherein the outer surface of the proximal portion of the distal sleeve element is positioned in threaded engagement with the inner surface of the distal portion of the intermediate sleeve element, wherein the inner surface of the distal portion of the distal sleeve element is positioned in threaded engagement with the outer surface of the proximal portion of the end cap.

9. The abutment system of claim 8, wherein the distal portions of the intermediate and distal sleeve elements have respective lengths relative to the common longitudinal axis, and wherein the length of the distal portion of the intermediate sleeve element is less than the length of the distal portion of the distal sleeve element.

10. The abutment system of claim 8, wherein the end cap comprises a prosthesis docking portion positioned between the proximal and distal portions of the end cap relative to the common longitudinal axis of the abutment system, wherein, upon threaded engagement between the outer surface of the proximal portion of the end cap and the inner surface of the distal sleeve element, the prosthesis docking portion of the end cap is flush with the outer surface of the distal portion of the distal sleeve element.

11. The abutment system of claim 8, wherein, following engagement between the intermediate sleeve element and the distal sleeve element, the outer surfaces of the distal portions of the intermediate and distal sleeve elements are flush.

12. The abutment system of claim 3, wherein the outer surface of the distal portion of the proximal sleeve element is sloped inwardly relative to the common longitudinal axis of the abutment system moving away from the proximal portion of the proximal sleeve element.

13. The abutment system of claim 3, wherein the proximal sleeve element comprises a lip circumferentially surrounding the central bore of the distal portion of the proximal sleeve element and protruding from the outer surface of the distal end portion relative to the common longitudinal axis of the abutment system.

14. The abutment system of claim 1, wherein the outer surface of the distal portion of at least one sleeve element of the plurality of sleeve elements comprises a porous material.

15. The abutment system of claim 1, wherein the outer surface of the distal portion of at least one sleeve element of the plurality of sleeve elements is configured to inhibit bio-adhesion.

16. The abutment system of claim 1, wherein the outer surface of the distal portion of at least one sleeve element of the plurality of sleeve elements is configured to promote bio-adhesion and soft-tissue integration.

17. The abutment system of claim 1, wherein at least a portion of the outer surface of the distal portion of each sleeve element of the plurality of sleeve elements comprises a porous material.

18. The abutment system of claim 1, wherein the outer surface of the distal portion of the proximal sleeve element comprises a first material, and wherein the outer surface of the distal portion of at least one other sleeve element of the plurality of sleeve elements comprises a material that is different from the first material.

19. The abutment system of claim 1, wherein the elongate shaft of the base element is integrally formed with the flange of the base element.

20. The abutment system of claim 1, wherein the elongate shaft of the base element is configured for removable coupling to the flange of the base element.

21. The abutment system of claim 1, wherein the end cap defines a cavity that receives a distal portion of the elongate shaft of the base element.

22. The abutment system of claim 1, wherein the distal end of the end cap is closed.

23. A method of operatively coupling an implant stem to a prosthesis positioned external to a selected bone of a subject, comprising:
positioning the implant stem within a prepared site of the selected bone and surrounding soft tissue of the subject, operatively coupling an abutment system to the implant stem, the abutment system positioned external to the bone but internal to the subject, the abutment system having a common longitudinal axis and comprising a plurality of interlocking sleeve elements and an end cap, the plurality of interlocking sleeve elements comprising a proximal sleeve element and a distal sleeve element, wherein the proximal sleeve element is operatively coupled to the implant stem, wherein each sleeve element of the plurality of sleeve elements is positioned in selective, removable engagement with adjacent sleeve elements of the plurality of sleeve elements, wherein the abutment system further comprises a base element having only one flange and an elongate shaft secured to the flange, the flange having a first surface, an opposed second surface, and an outer edge extending between the first and second surfaces, the first surface of the flange defining a proximal end of the base element, wherein the elongate shaft extends from a central portion of the flange away from the base element in a distal direction relative to the common longitudinal axis of the abutment system, wherein the elongate shaft is received within the central bore of each sleeve element of the plurality of sleeve elements, and wherein the outer surface of the distal portion of at least one sleeve element of the plurality of sleeve elements is configured to promote soft-tissue integration; positioning the end cap of the abutment system in engagement with the distal sleeve element of the plurality of sleeve elements; and securing the external prosthesis to the end cap of the abutment system.

24. The method of claim 23, further comprising:
selectively removing at least one sleeve element of the plurality of sleeve elements.

25. The method of claim 24, wherein the method does not comprise removal of the implant stem from the prepared site.

26. The method of claim 23, further comprising:
selectively replacing at least one original sleeve element of the plurality of sleeve elements with a corresponding substitute sleeve element.

27. The method of claim 26, wherein the outer surface of the distal portion of the at least one original sleeve element comprises a first material, and wherein the outer surface of the distal portion of the substitute sleeve element comprises a material that is different from the first material.

28. The method of claim 23, wherein the end cap has a closed distal end.

* * * * *

UNITED STATES PATENT AND TRADEMARK OFFICE
CERTIFICATE OF CORRECTION

PATENT NO. : 9,839,535 B2
APPLICATION NO. : 14/415939
DATED : December 12, 2017
INVENTOR(S) : Brian Mueller Holt et al.

It is certified that error appears in the above-identified patent and that said Letters Patent is hereby corrected as shown below:

In the Specification

In Column 1, Lines 18-22 replace:
--"This invention was made with the government support under W81XWH-06-1-0574 awarded by Army/MRMC–Medical Research and Material Command, and AR058356 awarded by National Institute of Health. The government has certain rights in the invention."--

With:
--"This invention was made with government support under Grant No. W81XWH-06-1-0574 awarded by the ARMY/MRMC and Grant No. AR058356 awarded by the National Institutes of Health. The government has certain rights in the invention."--

Signed and Sealed this
Twelfth Day of June, 2018

Andrei Iancu
*Director of the United States Patent and Trademark Office*